(12) United States Patent
Vleugels et al.

(10) Patent No.: US 7,300,450 B2
(45) Date of Patent: Nov. 27, 2007

(54) SURGICAL INSTRUMENT

(75) Inventors: Michel Petronella Hubertus Vleugels, Malden (NL); Markus Cornelis Jakobus Lazeroms, Riemst-Vroenhoven (BE)

(73) Assignee: VLEUGELS Holding B.V. (NL)

( * ) Notice: Subject to any disclaimer, the term of this patent is extended or adjusted under 35 U.S.C. 154(b) by 0 days.

(21) Appl. No.: 10/488,442

(22) PCT Filed: Sep. 3, 2002

(86) PCT No.: PCT/NL02/00574

§ 371 (c)(1),
(2), (4) Date: Sep. 7, 2004

(87) PCT Pub. No.: WO03/020139

PCT Pub. Date: Mar. 13, 2003

(65) Prior Publication Data
US 2005/0021078 A1    Jan. 27, 2005

(30) Foreign Application Priority Data
Sep. 3, 2001   (NL) .................................... 1018874

(51) Int. Cl.
*A61B 17/00* (2006.01)
(52) U.S. Cl. ............................ 606/205; 606/1; 606/46; 606/206; 606/207
(58) Field of Classification Search ................. 600/101, 600/117, 118; 606/1, 139, 147, 205
See application file for complete search history.

(56) References Cited

U.S. PATENT DOCUMENTS

| 5,389,849 A | 2/1995 | Asano et al. |
| 5,609,607 A | 3/1997 | Hechtenberg et al. |
| 5,965,880 A | 10/1999 | Wolf et al. |
| 6,436,107 B1 * | 8/2002 | Wang et al. ................. 606/139 |

FOREIGN PATENT DOCUMENTS

| EP | 1 125 557 | 8/2001 |
| WO | WO98/51451 | 11/1998 |
| WO | WO00/51486 | 9/2000 |

* cited by examiner

*Primary Examiner*—Linda C. M. Dvorak
*Assistant Examiner*—Matthew Kasztejna
(74) *Attorney, Agent, or Firm*—Keusey, Tutunjian & Bitetto, P.C.

(57) ABSTRACT

The invention relates to an instrument for surgery, in particular minimally invasive surgery. The instrument includes means for feeding back a force which is exerted on the working element of the instrument to the operating element. These means include at least a first force sensor for measuring the force which is exerted on the working element, a control unit and a first actuator. On the basis of a signal which originates from the first force sensor, the control unit controls at least the first actuator in order to control the operating element. Furthermore, the means preferably include a first position sensor for measuring a position of the working element with respect to the frame. The control unit advantageously determines an impedance which the working element is subject to as a result of the presence of a tissue or the like, on the basis of which impedance the control unit controls at least the first actuator.

18 Claims, 4 Drawing Sheets

SURGICAL INSTRUMENT

TECHNICAL FIELD OF THE INVENTION

The present invention relates to an instrument for surgery, in particular minimally invasive surgery, which instrument comprises an elongate frame which, in the vicinity of a first end thereof, comprises an operating element, which can be operated manually, and, at a second end thereof, at least one working element which can move with respect to the frame.

DESCRIPTION OF RELATED ART

An instrument of this type is used in particular in surgical procedures which use minimally invasive operating techniques. In a minimally invasive operation of this type, a number of small incisions are made and instruments and the like can be inserted through these incisions. Generally, a cylindrical tube is placed into the incision and the instruments are placed through it. The instruments which are used in principle correspond to the instruments which are used in conventional operating techniques. However, a narrow and elongate instrument is required in order to satisfy the specific requirements of the minimally invasive method, i.e. the instrument has to be placed through the relatively narrow tube, the working element projecting at one end of the tube while the operating element projects at the other end of the tube. A suitable instrument therefore comprises at least one elongate frame, a working element which can move with respect to the frame and an operating element, by means of which the working element of the instrument can be operated. The working element of the instrument may have various functions. For example, it can be used to clamp, grip, cut or staple. In cases which require a plurality of actions or instruments, two or more working elements which can move with respect to the frame will be used.

Minimally invasive operating techniques have the advantage that a smaller incision is required, and consequently there is generally less risk of infection and on average a shorter hospitalization is required.

In addition to the known benefits of the minimally invasive operating techniques, a number of drawbacks should also be mentioned. The surgeon does not have a direct view of the actions which he is carrying out. It is necessary to use cameras and television screens or the like to obtain the visual information which is directly available to him in conventional operating techniques. The specific shape of the instruments, i.e relatively narrow and elongate, which are used result in more friction in relative terms, and the instruments are more flexible, with the result that the mechanical feedback of the force exerted on the working element to the operating mechanism is less good. Consequently, the surgeon has less idea of the force which he is exerting by means of the working element of the instrument on something which is in the working element of the instrument. Consequently, it is possible, for example, that he may damage tissue as a result of clamping it too hard.

WO 98/11833 discloses an instrument for minimally invasive operating techniques in which the friction in the instrument is reduced compared to conventional designs through the use of rolling-contact bearings. This results in an improved mechanical feedback of the force which is exerted on the working element of the instrument. However, on account of the specific shape required for instruments for minimally invasive surgery, friction and hysteresis are still present in the design, and consequently the force which is exerted on the working element of the instrument is not correctly fed back to the operating mechanism of the instrument. As a result, the user of an instrument of this type does not have an optimum "feeling" for the tissue or the like which he is manipulating with the instrument. It is then difficult for a surgeon to position the working element of the instrument accurately.

The object of the invention is to provide an improved instrument for use in surgery, in particular minimally invasive surgery, which eliminates the above-mentioned drawback.

SUMMARY OF THE INVENTION

The object is achieved with an instrument according to the preamble of claim 1, characterized in that the instrument comprises means for feeding back a force which is exerted on the working element of the instrument to the operating element, which means comprise at least a first force sensor for measuring the force which is exerted on the working element, a control unit and a first actuator which is coupled to the operating element, the control unit controlling at least the first actuator on the basis of a signal which originates from the first force sensor.

By measuring the force which is exerted on the working element using a force sensor and feeding it back via a control unit to the operating element, the user can feel the force which is exerted by the working element without this feeling being influenced by friction and/or hysteresis in the instrument. The operating element is then, as it were, controlled by the first actuator.

The working element used in the instrument may have various functions. For example, it may be suitable for clamping, gripping, pinching or stapling or for holding a needle or the like. Often, there are two or more of these working elements which can move with respect to the frame. Furthermore, the instrument may be designed in such a manner that the working elements can be positioned exchangeably in the instrument.

The operating element is operated manually and is generally an operating handle as is present in a conventional surgical instrument. However, it is also possible for the operating element to be designed differently, for example as a rotary button or the like.

The surgical instrument is preferably to be held by hand.

The sensors, actuators and the control unit are preferably integrated in the instrument or secured directly to the instrument. As a result, the instrument remains easy to handle, so that the user finds it easy to use and can be very flexible in his movements. The instrument according to the invention can be designed advantageously with dimensions substantially corresponding to the dimensions of conventional minimally invasive instruments or an only slightly enlarged version thereof.

Preferably, the control unit determines an impedance to which the working element is subject, for example as a result of the presence of a tissue or the like, on the basis of the force which is exerted on the working element, the position in which the working element is located with respect to the frame and the speed at which the working element is moving with respect to the frame, the control unit controlling at least the first actuator on the basis of the impedance.

The impedance of a specific material is a good measure of the feeling provided by a material of this type when it is touched. The control unit according to the invention advantageously feeds the impedance to which the working element of the instrument is subject back to the operating element, so that the user has a very realistic "feeling" of the tissue or the like which is being manipulated by the working element.

The force which is exerted on the working element and the position of the working element with respect to the frame are determined with the aid of the first force sensor and first position sensor respectively. The speed of the working element is preferably determined by the derivative over the course of time of the position signal measured by the first position sensor, but it is also possible, by way of example, to determine the speed using a separate speed sensor.

In a preferred embodiment, the instrument has a connecting rod or the like which is coupled to the working element and to the operating element in order to drive the working element.

This results in what is known as a semi-active instrument, in which the working element at the end of the frame is driven directly, i.e. via a mechanical connection, by the surgeon, while the control unit uses the first actuator to control the operating element on the basis of the detected impedance.

In another preferred embodiment, the instrument has a connecting rod or the like which is coupled to the working element in order to drive the working element, the connecting rod or the like being driven by a second actuator which is controlled by the control unit.

In what is known as a fully active instrument of this type, the controls of the operating movements of the surgeon and the movement of the working element pass via the control unit. The control unit controls the two actuators on the basis of signals which are obtained from the force and position sensors.

The control unit preferably determines an impedance to which the operating element is subject on the basis of the force which is exerted on the operating element, the position and speed of the operating element, which impedance is likewise fed back to the actuators. In this way, the feedback of feeling is improved still further. In this case, the force on the operating element and the position of the operating element are measured by means of a second force sensor and position sensor, respectively. The speed is preferably determined as a derivative over the course of time of the position signal measured by the second position sensor.

Advantageously, at least one of the force sensors and/or position sensors comprises a glass fibre, whereby a light source and a light sensor are positioned in the vicinity of a first end of the glass fibre, and whereby a reflective surface, which moves as a function of the position and/or force which is to be measured, is arranged at a distance from a second end of the glass fibre. The force and/or position sensors make use of glass fibres and reflective surfaces; the extent to which light which originates from the light source and emerges from the second end of the glass fibre is reflected into the second end of the glass fibre being representative of the force or position which is to be measured. The amount of light which is reflected is in this case detected by the light sensor.

Sensors of this type have the advantage over more conventional sensors in that no electrical signals are used at least in the vicinity of the working element. The use of electrical signals is undesirable, since the measurement signals from the sensors may be interfered with by other equipment present in the operating theater. Moreover, glass fibres are inexpensive and take up little space.

In a force sensor, the second end of the glass fibre and the reflective surface are fixed to the working element. A force exerted on the working element will cause this working element to bend slightly or change its shape in some other way. This bending or other change in shape will change the position and/or orientation of the reflective surface with respect to the second end of the glass fibre. As a result, the extent to which light which emerges from the second end of the glass fibre is reflected into the second end of the glass fibre will change. The force exerted on the working element can be determined on the basis of this change in the amount of light which is reflected.

The position of the working element can be determined in a corresponding way using a position sensor. In a position sensor, of this type, however, the second end of the glass fibre is not arranged on the working element, but rather on the frame, so that the level of reflection depends on the position of the working element with respect to the frame.

As an alternative to glass fibres, incidentally, it is also possible to use other suitable light conductors.

Advantageously, the instrument comprises at least two parts which can be detached from one another, of which one part is suitable for reuse, generally after sterilization, and another part is suitable for single use, which two parts can be coupled to one another by means of a coupling.

The use of glass fibres makes the instrument as a whole more difficult to sterilize, since the glass fibres are damaged by heating. However, making the instrument disposable makes use of the instrument very expensive, on account of the electronics required for the control unit and the light sensor(s) and the actuators. By separating the expensive components, in particular electronics and actuators, of the instrument from the section of the instrument in which the glass fibres run, it is possible for the instrument to be kept in use reliably and inexpensively.

A particular advantage is that with the instrument it is possible to record data which are measured by the various sensors. Data of this type may be important for the development of computer models which are used, for example, in simulation training exercises or the like. For this purpose, a surgical simulator comprises an operating element which can be operated manually, a first actuator for controlling the operating element by means of a force, and control means which are designed to control the first actuator on the basis of an impedance from an actual surgical procedure carried out using an instrument as described above. The use of the instrument according to the invention in a specific surgical intervention can therefore be practiced by simulating the working element and the forces exerted on it with the aid of the control means. In this case, the first actuator can be controlled in the same way as if it were being controlled by the control unit of the instrument, and the above-mentioned second force sensor and second position sensor can also be used in corresponding ways. Also, the operating section of the instrument can be used in a telesurgery instrument, comprising an operating element which can be operated manually, a first actuator for controlling the operating element by means of a force, and control means which are designed to control the first actuator on the basis of an impedance from a surgical procedure carried out remotely. In this case too, the first actuator can be controlled in the same way as if it were being controlled by the control unit of the instrument, and the above-mentioned second force sensor and second position sensor can also be used in a corresponding way.

Furthermore, the invention relates to a force sensor in accordance with claim 18 and to a position sensor in accordance with claim 19. Preferred embodiments of the force sensor and position sensor can be designed in accordance with the ways which have been explained in more detail for the force and position sensors for the instrument according to the invention.

BRIEF DESCRIPTION OF THE DRAWINGS

Further characteristics and advantages of the instrument according to the invention will be explained in more detail below with reference to a number of embodiments which are illustrated in the appended drawings, in which.

Throughout the various figures, the same reference numerals are used to refer to corresponding components or components which have a corresponding action.

DETAILED DESCRIPTION OF PREFERRED EMBODIMENTS

Figure 1:
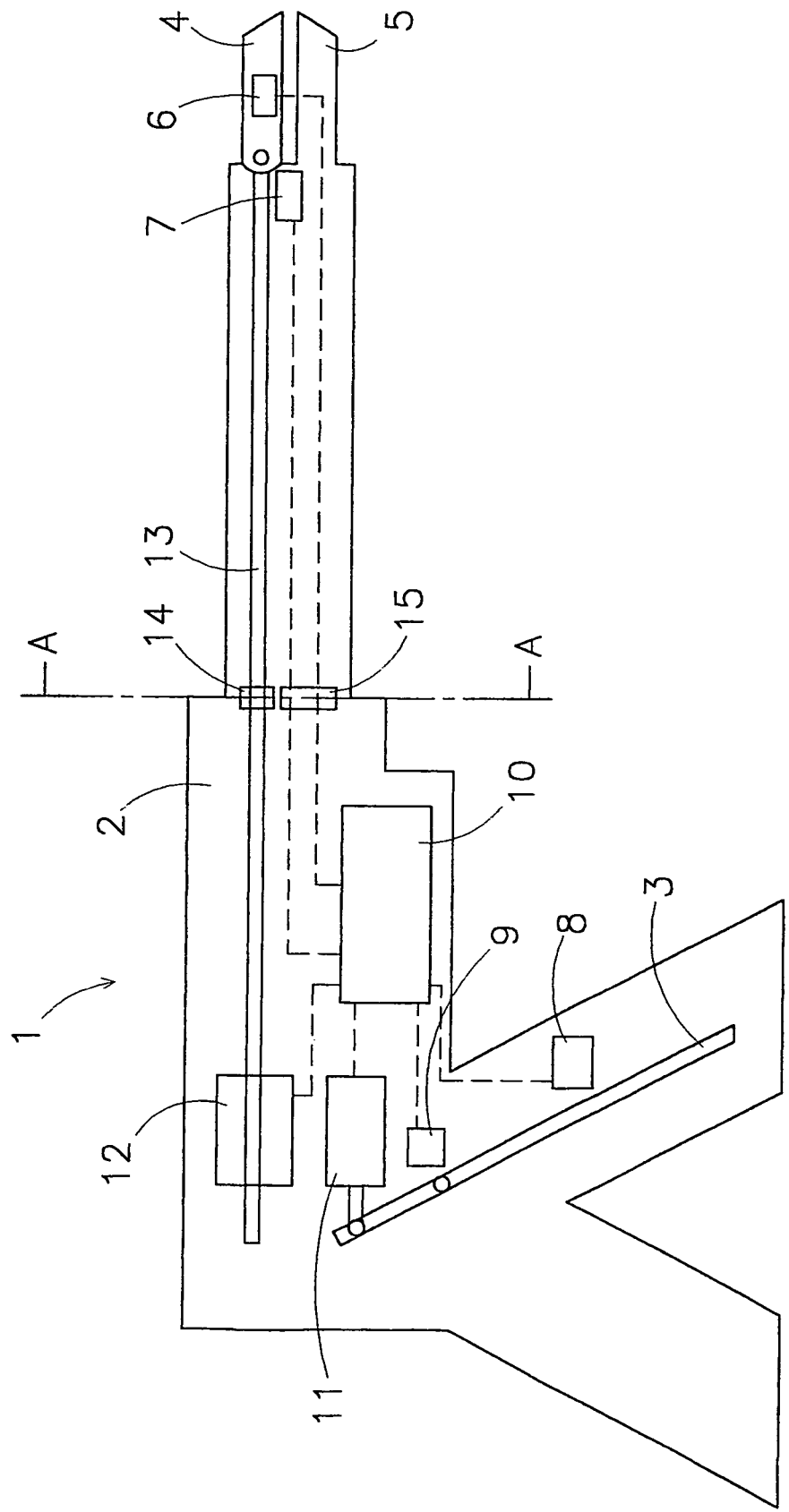
FIG. 1 diagrammatically depicts a first preferred embodiment of an instrument according to the invention, FIG. 2 diagrammatically depicts a second preferred embodiment of an instrument according to the invention, FIG. 3 diagrammatically depicts a force sensor of an instrument according to the invention, and FIG. 4 diagrammatically depicts a position sensor of an instrument according to the invention.

FIG. 1 shows a first preferred embodiment of the instrument according to the invention, denoted overall by reference numeral 1. The various components of the instrument 1 are diagrammatically depicted in the figure. The instrument 1 comprises an elongate frame 2 having, at a first end, at least one operating element 3 and, at the second end, a working element 4 which is moveably secured to the frame and a second working element 5 which in this case is fixed to the frame and forms a component thereof. It is also possible to make a second working element moveable with respect to the frame and to provide more than two fixed or moveable working elements.

A force sensor 6 for measuring the force which is exerted on the working element 4 and a position sensor 7 for measuring the position of the working element 4 with respect to the frame 2 are also arranged in or close to the working element 4. A force sensor 8 for measuring the force which is exerted on the operating element and a position sensor 9 for measuring the position of the operating element with respect to the frame are arranged in or close to the operating element 3. The measured signals from the force sensors 6, 8 and position sensors 7, 9 are transmitted to a control unit 10.

The force sensors 6, 8 and position sensors 7, 9 may be conventional sensors which, by way of example, use strain gauges, potentiometers or the like. For in particular the sensors which are positioned in or close to the working element 4, it is preferable to use sensors in which glass fibres are used. Sensors of this type are less sensitive to interference than electrical sensors and will be described in more detail below.

The instrument 1 also comprises an actuator 11 which is coupled to the operating element 3 and an actuator 12 which drives a connecting rod 13 to which the working element 4 is coupled. The actuators can be controlled independently of one another by the control unit. The actuators are preferably linear electromagnetic actuators.

In the control unit 10, the impedance to which the working element 4 is subject is determined on the basis of the force which is exerted on the working element 4, the position of the working element 4 and the speed of the working element 4. An impedance to which the operating element is subject is also determined on the basis of the force to which the operating element is subject, the position of the operating element and the speed of the operating element. The speeds are in this case calculated by taking the derivative over time of the signal from the position sensors. The two actuators 11, 12 are controlled by the control unit 10 on the basis of the two impedances which have been determined.

The instrument 1 comprises at least two parts which can be detached from one another, of which a reusable part is suitable for reuse after sterilization and another, disposable part is suitable for single use. The two parts which can be separated from one another are indicated by line A-A in the figure. The two parts can be coupled to one another by means of a coupling. The coupling comprises a mechanical coupling 14 for driving the connecting rod 13 in the disposable part. There is also an optical coupling 15 for coupling optical information, i.e coupling the glass fibres in the disposable part to opto-electronic means, such as the light sensor and the light source.

The reusable part comprises the actuators 11, 12, the control unit 10, the light source, the light sensor, which are preferably accommodated in a watertight housing, so that they are protected from moisture and the like.

Figure 2:
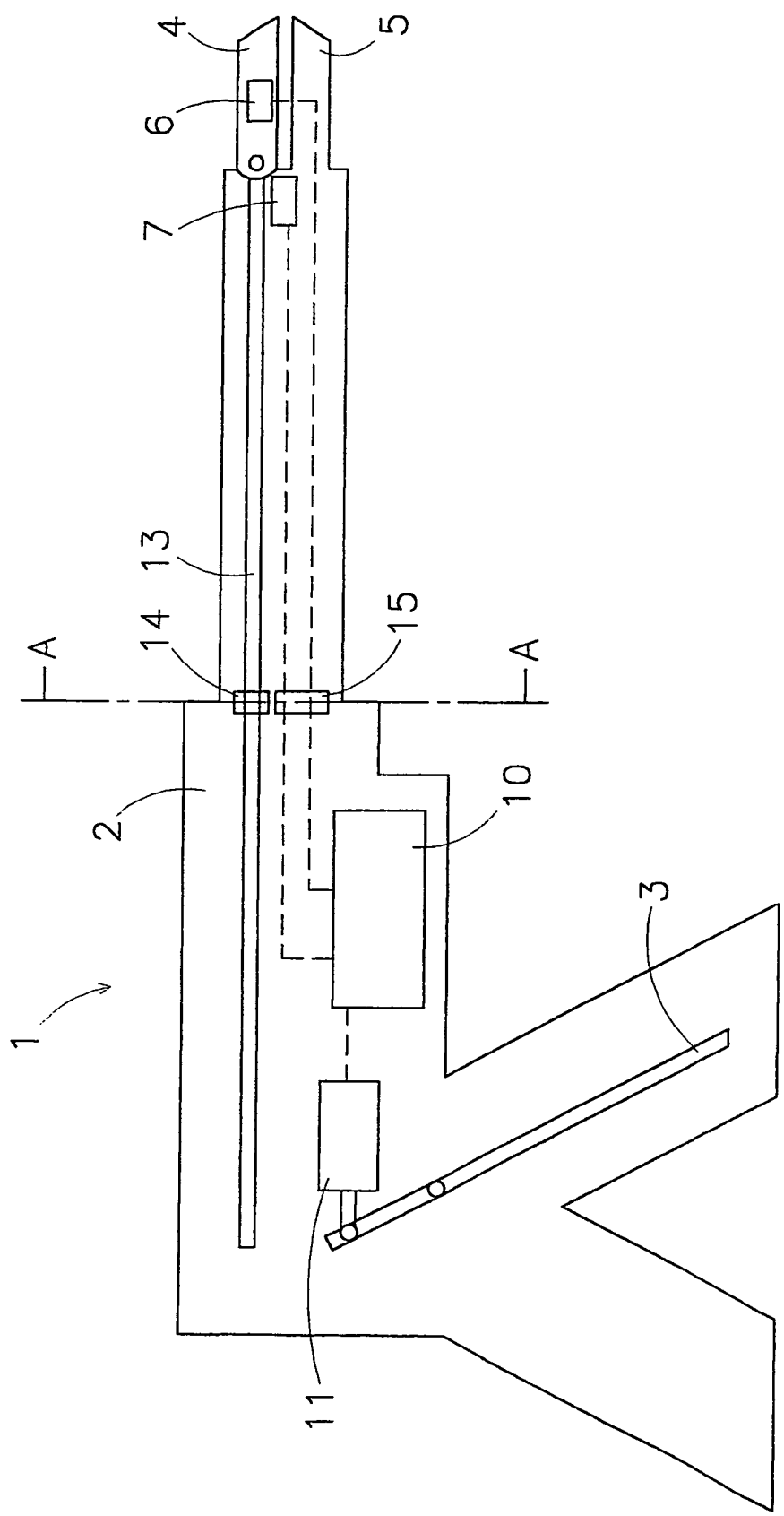

A second preferred embodiment of the instrument according to the invention is shown in FIG. 2. In this case, the connecting rod 13 is directly mechanically coupled to the operating element 3. The force which the user exerts on the operating element 3 is transmitted directly to the working element 4 via the connecting rod 13. A force sensor 6 and a position sensor 7 are arranged in or close to the working element 4. The signals from the force sensor 6 and the position sensor 7 are transmitted to a control unit 10 which controls an actuator 11 which is coupled to operating element 3. The control unit 10 controls the actuator 11, with a view to controlling the operating handle, on the basis of the impedance which is determined in the control unit by means of the measured position and force and the calculated speed. As a result, the user is provided with good feedback about the way in which he is manipulating a tissue or the like using the working element.

The instrument 1 is composed of a disposable part and a reusable part which comprises a coupling in the region of line A-A. The coupling has a mechanical coupling 14 for driving the working element 4 and an optical coupling 15 for transmitting optical information.

Figure 3:
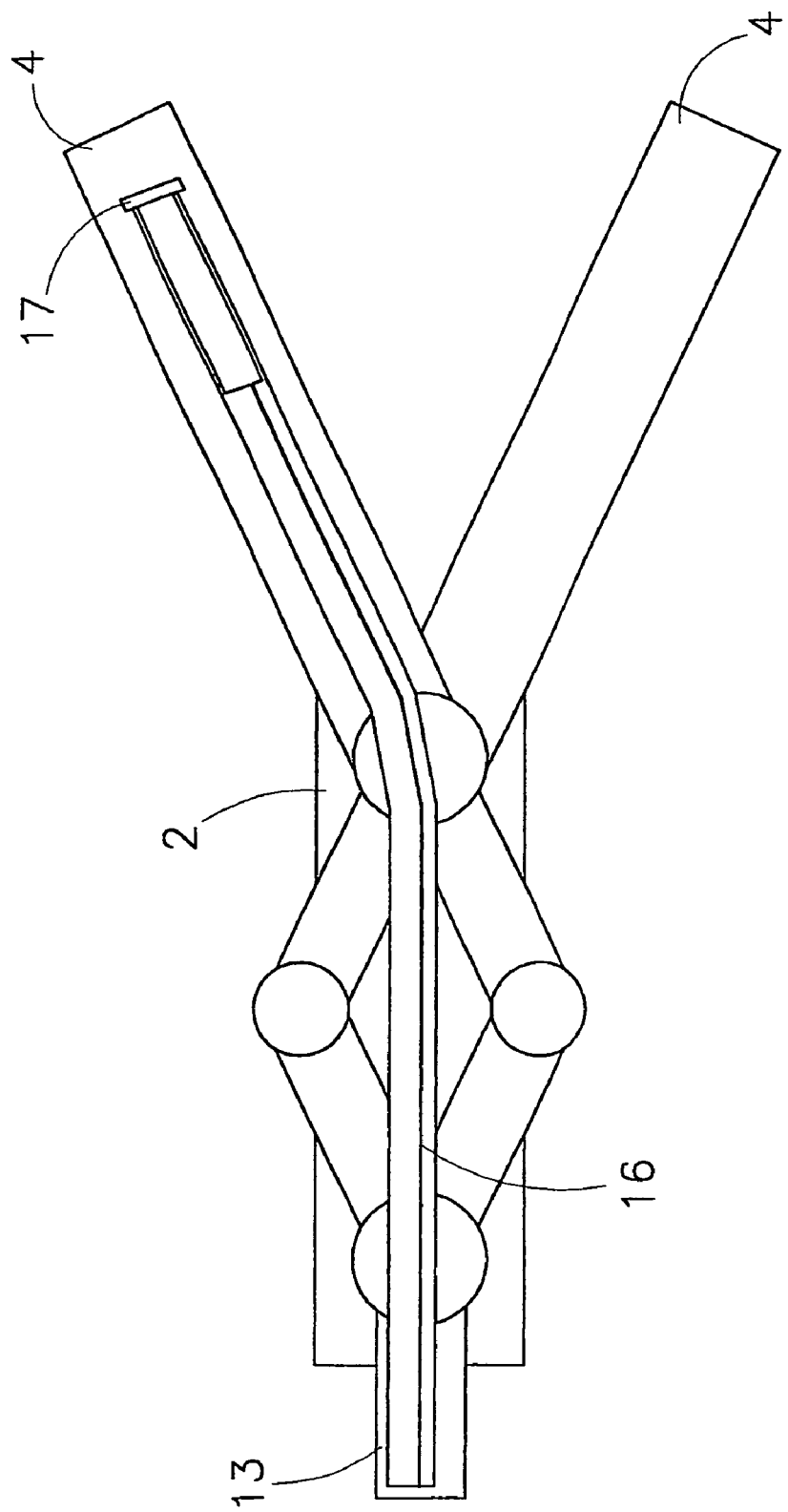

FIG. 3 shows at least part of a preferred embodiment of the force sensor of the instrument according to the invention, which force sensor comprises a glass fibre. The figure shows one end of an instrument, where two working elements 4 which can move with respect to the frame and form a clamping jaw, are arranged. The clamping jaw is opened by moving the connecting rod 13 in the direction of the clamping jaw, and the clamping jaw is closed by moving the connecting rod 13 away from the clamping jaw. One end of a glass fibre 16 extends at least part way into one of the working elements 4. A light source and a light sensor (neither of which is shown) are arranged in the vicinity of the other end of the glass fibre 16. The light source emits light through the glass fibre 16, and the light source detects the light which returns through the glass fibre 16.

In the vicinity of the end of a working element 4 of the clamping jaw which is remote from the instrument, there is a reflective surface 17 which at least partially reflects light which emerges from the end of the glass fibre 16 into the glass fibre 16. The reflective surface is positioned at a set distance from the end of the glass fibre 16. If a force is then exerted on the working element 4, the working element 4 will bend slightly. The result of this bending is that the amount of light which is reflected by the reflective surface 17 into the glass fibre 16 changes. This change, which is detected by the light sensor, is a measure of the force which is exerted on the working element 4. The amount of light which is measured is converted by the light sensor into an electrical signal which is representative of the force exerted on the instrument. This signal is transmitted to the control unit 10.

Figure 4:
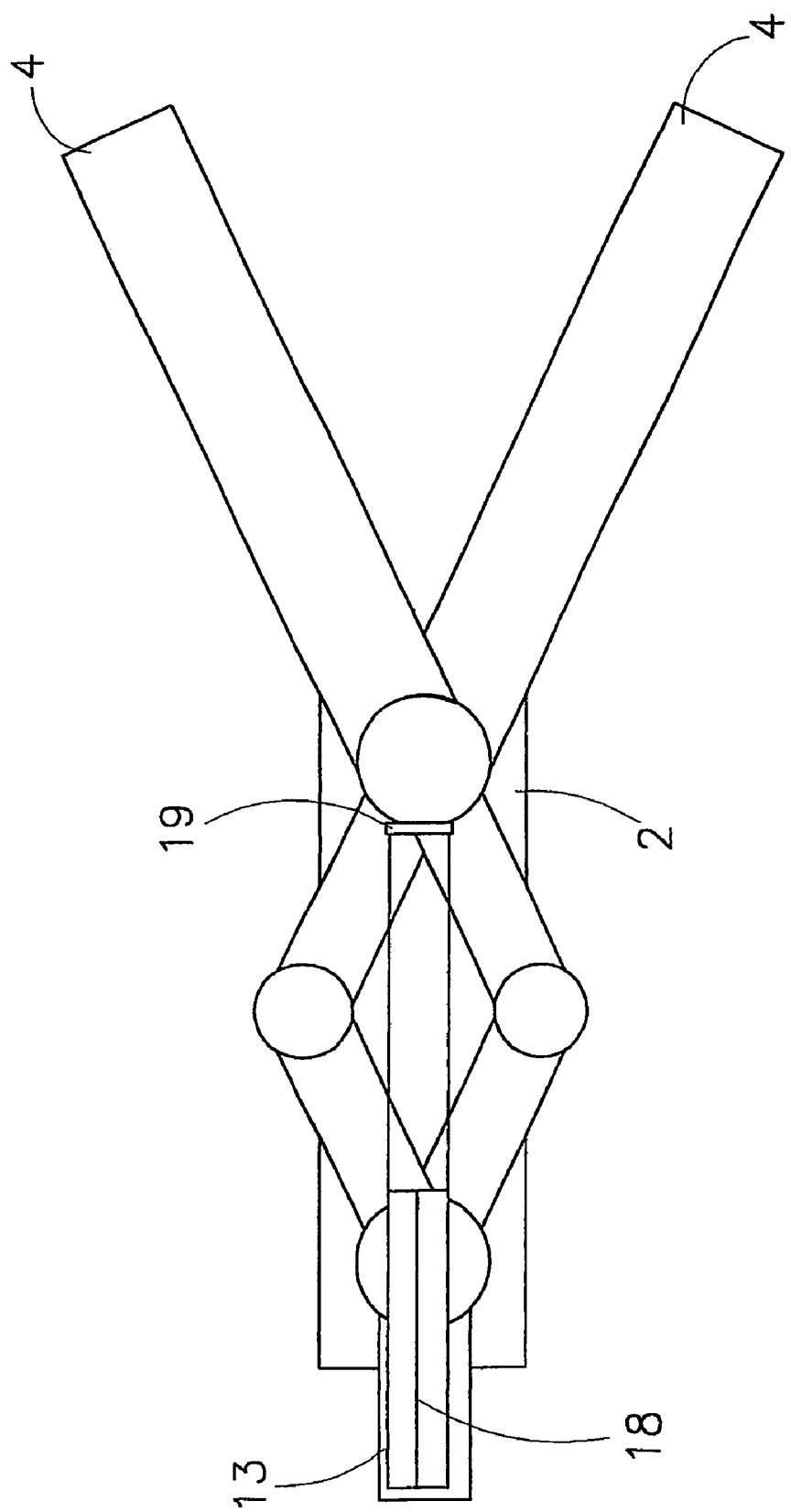

FIG. 4 shows at least part of a preferred embodiment of the position sensor of the instrument according to the invention, which position sensor comprises a glass fibre 18. The figure shows an end of an instrument corresponding to FIG. 3. The glass fibre 18 is secured to the frame 2 of the instrument 1. One end is directed towards a reflective surface 19 which is secured to one of the working elements 4. The light which is emitted by a light source (not shown) arranged at the other end of the glass fibre is at least partially reflected by the reflective surface 19 into the glass fibre 18. If the clamping jaw is moved with respect to the frame 2, more or less light is reflected into the glass fibre 18. The amount of light which is reflected and which is detected by the light sensor is a measure of the position of a working element 4 of the clamping jaw with respect to the frame 2. On the basis of the amount of light received, the light sensor emits an electrical signal, which is representative of the position of the working elements 4, to the control unit 10.

The invention claimed is:

1. An instrument for surgery, in particular minimally invasive surgery, said instrument comprising:
an elongate frame which, in the vicinity of a first end thereof, comprises an operating element (3), and, at a second end thereof, at least one working element (4), characterized in that the instrument (1) comprises means for feeding back a force which is exerted on the working element (4) of the instrument to the operating element (3), which means comprise at least a first force sensor (6) for measuring the force which is exerted on the working element, a control unit (10) and a first actuator (11) which is coupled to the operating element, the control unit being configured to control at least the first actuator (11) on the basis of a signal which originates from the first force sensor, wherein the first force sensor (6) comprises a glass fiber (16) configured to guide optical signals to and from the working element (4), whereby a light source and a light sensor are arranged in the vicinity of a first end of the glass fiber, and a second end of the glass fiber is fixed to the working element (4), and whereby a reflective surface (17) is arranged on the working element (4) at a defined distance from the second end of the glass fiber, which reflective surface reflects at least a proportion of the light which originates from the light source and emerges from the second end of the glass fiber into the second end of the glass fiber.

2. The instrument according to claim 1, characterized in that the instrument (1) has a connecting rod (13), which is coupled to the working element (4) and to the operating element (3) in order to drive the working element.

3. The instrument according to claim 1, characterized in that the instrument (1) has a connecting rod (13) which is coupled to the working element (4) in order to drive the working element, the connecting rod being driven by a second actuator (12) which is controlled by the control unit (10).

4. The instrument according to claim 3, characterized in that the control unit (10) determines an impedance to which the operating element (3) is subject on the basis of the force which is exerted on the operating element, the position in which the operating element is located with respect to the frame (2) and a speed at which the operating element is moving with respect to the frame, the control unit controlling the actuators (11, 12) on the basis of the impedance to which the working element (4) is subject and the impedance to which the operating element is subject.

5. The instrument according to claim 3, characterized in that the actuators (11, 12) are electromagnetic linear actuators.

6. The instrument according to claim 1, characterized in that the instrument (1) comprises at least two parts which are detachable from one another, of which one part is suitable for reuse and another part is suitable for single use, said two parts being coupleable to one another by means of a coupling.

7. The instrument according to claim 6, characterized in that the coupling comprises a mechanical coupling (14) and an optical coupling (15).

8. The instrument according to claim 6, characterized in that the part which is suitable for reuse comprises at least actuators (11, 12), the control unit (10), a light source, a light sensor and the operating element (3), and in that the part which is suitable for single use comprises at least the working element (4) and glass fibers (16, 18).

9. The instrument according to claim 8, characterized in that the actuators (11, 12), the control unit (10), the light source and the light sensor are accommodated in a water-tight enclosure.

10. The instrument of claim 1, wherein the at least one working element is moveable with respect to the frame.

11. The instrument of claim 1, wherein the operating element is manually operable.

12. The instrument according to claim 1, wherein the first end of the glass fiber is located spaced from the working element.

13. The instrument according to claim 1, wherein the means further comprise a first position sensor (7) configured for measuring a position of the working element (4) with respect to the frame (2).

14. The instrument according to claim 13, characterized in that the means further comprise a second force sensor (8) for measuring a force which is exerted on the operating element (3) and a second position sensor (9) for determining a position of the operating element with respect to the frame.

15. The instrument according to claim 14, characterized in that at least one of the force sensors (6, 8) and position sensors (7, 9) comprises a glass fiber, whereby a light source and a light sensor are positioned in the vicinity of a first end of the glass fiber, and whereby a reflective surface, which moves as a function of the position and/or force which is to be measured, is arranged at a distance from a second end of the glass fiber.

16. The instrument according to claim 13, characterized in that the first position sensor (7) comprises a glass fiber (18), whereby a light source and a light sensor are positioned in the vicinity of a first end of the glass fiber, and a second end of the glass fiber is arranged on the frame, and whereby a reflective surface (17) which is positioned at a certain distance from the second end of the glass fiber is arranged on the working element (4), which reflective surface (19) at least partially reflects light which originates from the light source and emerges from the second end of the glass fiber into the second end of the glass fiber.

17. The instrument according to claim 1, wherein the control unit (10) is configured to determine an impedance to which the working element (4) is subject on the basis of the force which is exerted on the working element, the position in which the working element is located with respect to the frame (2), and a speed at which the working element is moving with respect to the frame, the control unit being configured to control at least the first actuator (11) on the basis of the impedance.

18. The instrument according to claim 1, wherein the force exerted on the working element is determined based on a change in the amount of light which is reflected back into said second end of the glass fiber.

\* \* \* \* \*